United States Patent
Schwartz et al.

(10) Patent No.: US 9,164,106 B2
(45) Date of Patent: Oct. 20, 2015

(54) DETERMINATION OF DECREASED METABOLISM OF TRYPTOPHAN IN DIAGNOSIS OF AUTISM SPECTRUM DISORDERS

(71) Applicant: Greenwood Genetic Center, Inc., Greenwood, SC (US)

(72) Inventors: Charles E. Schwartz, Greenwood, SC (US); Luigi Boccuto, Greenwood, SC (US)

(73) Assignee: GREENWOOD GENETIC CENTER, INC., Greenwood, SC (US)

( * ) Notice: Subject to any disclaimer, the term of this patent is extended or adjusted under 35 U.S.C. 154(b) by 136 days.

(21) Appl. No.: 13/835,115

(22) Filed: Mar. 15, 2013

(65) Prior Publication Data

US 2013/0244273 A1 Sep. 19, 2013

Related U.S. Application Data

(60) Provisional application No. 61/611,131, filed on Mar. 15, 2012.

(51) Int. Cl.
*C12N 5/00* (2006.01)
*G01N 33/68* (2006.01)
*C12N 15/10* (2006.01)

(52) U.S. Cl.
CPC ........ *G01N 33/6896* (2013.01); *C12N 15/1082* (2013.01); *C12N 2502/11* (2013.01)

(58) Field of Classification Search
CPC .... C12N 15/1082; C12N 15/85; C12N 15/63; C12N 9/22; C12N 15/8509; C12N 15/86; C12N 15/113; C12N 15/907; C12N 2310/10; C12N 2310/3519; C12N 2310/531; C12N 15/01; C12N 15/70; C12N 15/74; C12N 2800/101; C12N 15/00
See application file for complete search history.

(56) References Cited

U.S. PATENT DOCUMENTS

2007/0248947 A1* 10/2007 Cezar ................................ 435/4

OTHER PUBLICATIONS

Kocki et al. E Journal of Pharmacology 541 (2006) 147-151.*
Chugani. M R and Dev Dis Research Review 10:112-116 (2004).*
Investigators:, A.a.D.D.M.N.S.Y.P. & (CDC), C.f.D.C.a.P. "Prevalence of Autism Spectrum Disorders—Autism and Developmental Disabilities Monitoring Network, United States, 2006". MMWR Surveillance Summaries, 2009, 58, 10, 1-20.
Ganz, "The Lifertime Distribution of the Incremental Societal Costs of Autism", Arch Pediatr Adolesc Med., 2007, 161, 4, 343-349.
Anderson, "Genetics of Childhood Disorders: XLV. Autism, Part 4: Serotonin in Autism". Journal of the American Academy of Child and Adolescent Psychiatry, 2002, 41, 12, 1513-1516.
Yap, I.K. et al., "Urinary metabolic phenotyping differentiates children with autism from their unaffected siblings and age-matched controls". J Proteome Res 9 (6), 2996-3004 (2010).
Adams et al., "Nutritional and metabolic status of children with autism vs. neurotypical children, and the association with autism severity", Nutrition & Metabolism, 2011, 8, 1-32.
Bochner et al, "Assay of the Multiple Energy-Producing Pathways of Mammalian Cells". PLoS One, 2011, 6, 3, 1-8.
Schroer et al, "Autism and maternally derived aberrations of chromosome 15q". American Journal of Medical Genetics, 1998, 76, 4, 327-336.
Witten et al, "Data Mining: Practical Machine Learning Tools and Techniques". (Morgan Kaufman, San Francisco, 2005).
Smalley et al, "Autism and Genetics". Arch. Gen Psychiatry, 1988, 45, 10, 953-961.
Ritvo et al, "The UCLA-University of Utah epidemiologic survey of autism: recurrence risk estimates and genetic counseling". The American journal of psychiatry, 1989, 146, 8, 1032-1036.
Schaefer et al, "Clinical genetics evaluation in identifying the etiology of autism spectrum disorders." Genetics in Medicine, 2008, 10, 4, 301-305.
Miles, "Autism spectrum-disorders—a genetics review". Genetics in Medicine, 2011, 13, 4, 278-294.
Smith et al., "Nuclear and mitochondrial genome defects in autisms". Annals of the New York Academy of Sciences, 2009, 1151, 102-132.
Giulivi et al., "Mitochondrial dysfunction in autism". JAMA, 2010, 304, 21, 2389-2396.
Rossignol et al., "Mitochondrial dysfunction in autism spectrum disorders: a systematic review and meta-analysis". Molecular Psychiatry, 2012, 17, 290-314.
Mattson et al., "Energetics and Oxidative Stress in Synaptic Plasticity and Neurodegenerative Disorders". NeuroMolecular Medicine, 2002, 2, 215-231.
Anderson et al., "Bridging from Cells to Cognition in Autism Pathophysiology: Biological Pathways to Defective Brain Function and Plasticity". Am. J. Biochem. & Biotech., 2008, 4, 2, 167-176.
Pastural et al., "Novel plasma phospholipid biomarkers of autism: Mitochondrial dysfunction as a putative causative mechanism". Prostaglandins, Leukotrienes and Essential Fatty Acids, 2009, 81, 4, 253-264.
Rubenstein et al., "Model of autism: increased ratio of excitation/inhibition in key neural systems". Genes, Brain and Behavior, 2003, 2, 255-267.
Bourgeron, "A synaptic trek to autism". Current Opinion in Neurobiology, 2009, 19, 2, 231-234.
Kelleher et al., "The Autistic Neuron: Troubled Translation?". Cell, 2008, 135, 401-406.

(Continued)

*Primary Examiner* — Blaine Lankford
(74) *Attorney, Agent, or Firm* — Dority & Manning, P.A.

(57) ABSTRACT

Methods for diagnosis of autism spectrum disorders are described. Methods include culturing a cell sample of a test subject with a tryptophan-containing energy source and examining the culture to determine the ability of the cells of the test subject to properly metabolize tryptophan. A determination that a subject does not properly metabolize tryptophan is an indication that the subject may be afflicted with autism. Methods can be utilized as a quick and reliable diagnostic tool for autism spectrum disorders and may provide a unifying model for the genetic heterogeneity of autism spectrum disorders.

11 Claims, 4 Drawing Sheets

(56) References Cited

OTHER PUBLICATIONS

Mostafa et al., "Polyunsaturated fatty acids, carnitine and lactate as biological markers of brain energy in autistic children". Int. J. of Child Neuropsychiatry, 2005, 2, 179-188.

James et al., "Metabolic endophenotype and related genotypes are associated with oxidative stress in children with autism". Am. J. Med. Genetic Part B (Neuropsychiatric Genetics), 2006, 141B, 8, 947-956.

Geier et al., "Biomarkers of environmental toxicity and susceptibility in autism", Journal of the Neurological Sciences, 2009, 280, 101-108.

Stone et al, "Endogenous kynurenines as targets for drug discovery and development". Nature Reviews Drug Discovery. 2002, 1, 609-620.

Casanova, "The Neuropathology of Autism". Brain Pathol., 2007, 17, 422-433.

Courchesne et al., "Neuron number and size in prefrontal cortex of children with autism". JAMA, 2011, 306, 18, 2001-2010.

Kurup et al., "A Hypothalamic Digoxinmediated Model for Autism". Int. J. Neurosci., 2003, 113, 11, 1537-1559.

Sweeten et al., "High Nitric Oxide Production in Autistic Disorder: A Possible Role for Interferon-γ". Biol. Psychiatry, 2004, 55, 434-437.

Sogut et al., "Changes in nitric oxide levels and antioxidant enzyme activities may have a role in the pathophysiological mechanisms involved in autism". Clin. Chim. Acta., 2003, 331, 111-117.

Zoroglu et al., "Pathophysiological role of nitric oxide and adrenomedullin in autsim". Cell Biochem Funct, 2003, 21, 55-60.

Gingrich et al., "Dissecting the role of the serotonin system in neuropsychiatric disorders using knockout mice". Psychopharmacology, 2001, 155, 1-10.

Barnes et al., "A review of central 5-HT receptors and their function", Neuropharmacology, 1999, 38, 1083-1152.

Chugani et al., "Developmental changes in brain serotonin synthesis capacity in autistic and nonautistic children". Ann Neurol, 1999, 45, 287-295.

Schaechter et al., "Serotonin release varies with brain tryptophan levels". Brain Research, 1990, 532, 203-210.

Moskowitz et al., "The Effect of Trytophan on Social Interaction in Everyday Life: A Placebo-Controlled Study". Neuropsychopharmacology, 2001, 25, 2, 277-289.

aan het Rot et al., "Social behaviour and mood in everyday life: the effects of tryptophan in quarrelsome individuals". J Psychiatry Neurosci, 2006, 31, 4, 253-262.

Johansson et al., "Altered trytophan and alanine transport in fibroblasts from boys with attention-deficit/ hypercativity disorder (ADHD): an in vitro study". Behavioral and Brain Functions 2011, 7, 40, 1-7.

Sugden et al., "Genes within the serotonergic system are differentially expressed in human brain". BMC Neuroscience 2009, 10, 50, 1-11.

Zill et al., "Analysis of tryptophan hydrozylase I and II mRNA expression in the human brain: A post-mortem study". Journal of Psychiatric Research, 2007, 41, 168-173.

Daubert et al., "Serotonin: a regulator of neuronal morphology and circuitry", Trends in Neurosciences, 2010, 33, 9, 424-434.

Bonnin et al., "A Transient placental source of serotonin for the fetal forebrain". Nature, 2011, 472, 347-350.

Voineagu et al., "Transcriptomic analysis of autistic brain reveals convergent molecular pathology". Nature, 2011, 474, 380-384.

Casanova et al., "Minicolumnar abnormalities in autism". Acta Neuropathol, 2006, 112, 287-303.

Minshew et al., "The New Neurobiology of Autsism: Cortex, Connectivity, and Neuronal Organization". Arch Neurol, 2007, 64, 7, 945-950.

Putluri et al., "Metabolomic Profiling Reveals a Role for Androgen in Activating Amino Acid Metabolism and Methylation in Prostate Cancer Cells". PLoS One, 2011, 6, 7, e21417.

Tusher et al., "Significance analysis of microarrays applied to the ionizing radiation response". PNAS, 2001, 98, 9, 5116-5121.

Storey et al., "Statistical significance for genomewide studies". PNAS, 2003, 100, 16, 9440-9445.

Sokal et al., "Biometry: the principles and practice of statistics in biological research". $3^{rd}$ ed. (Freeman, New York, 1995).

Chen et al., "Regulation of Cellular Metabolism and Cytokines by the Medicinal Herb Feverfew in the Human Monocytic THP-1 Cells". Evid Based Complement Alternat Med, 2009, 6, 91-98.

* cited by examiner

DETERMINATION OF DECREASED METABOLISM OF TRYPTOPHAN IN DIAGNOSIS OF AUTISM SPECTRUM DISORDERS

PRIORITY INFORMATION

The present application claims priority to U.S. Provisional Patent Application Ser. No. 61/611,131 of Schwartz, et al. titled "Determination of Decreased Metabolism of Tryptophan in Diagnosis of Autism Spectrum Disorders" filed on Mar. 15, 2012, which is incorporated by reference herein.

BACKGROUND

Autism spectrum disorders (ASDs also collectively referred to herein as autism) include a group of serious and enigmatic neurobehavioral disorders that usually become apparent early in childhood and persist as lifelong disabilities. Disturbances in three categories of behavior (reciprocal social interactions, verbal and nonverbal communications, and age appropriate activities and interests) are considered hallmarks of ASDs. The conditions encompassed in ASDs can have a tremendous impact on society and families as affected individuals utilize a wide range of services and considerable resources, particularly considering that patients diagnosed with autism often reach adulthood and require special assistance for their entire life span.

The number of children diagnosed with ASDs has greatly increased in recent decades. At the midpoint of the 20th Century, autism was narrowly defined and uncommonly diagnosed (with a prevalence of about four per 10,000). Greater awareness, availability of services, changes in diagnostic criteria to include a broader spectrum of neurodevelopmental abnormalities, and possibly other factors have contributed to the ten-fold or greater increase in the frequency with which ASDs are diagnosed. One extraordinary aspect of the epidemiology is the three-fold to six-fold excess of males. The prevalence of ASDs is currently considered to be about 1% in the U.S. population under 8 years of age.

ASDs appear causally heterogeneous, which makes clear understanding and diagnosis of the conditions more difficult. Although scientists have long abandoned the idea that autism is caused by humorless and rigid parenting, they have been unable to identify specific cause(s) in any substantial proportion of cases. Standardized criteria for autism as defined in the Diagnostic and Statistical Manual, IVth Edition (DSM IV-TR) may be assessed based on parental, caregiver, and/or examiner observations using the Autism Diagnostic Interview, Revised (ADI-R) and Autism Diagnostic Observation Schedule (ADOS). Such diagnosis is typically not performed before the age of 3, even if recent progress has allowed diagnosis at an earlier age.

Only meager evidence exists to suggest that environmental insults play a significant role in the causation of autism. Prenatal and postnatal infections (rubella, cytomegalovirus, herpes) have been documented in a few cases. Little evidence exists to suggest injury in the perinatal period as a causative factor, although low birth weight and premature birth has been noted as a risk factor (Schendel, et al. 2008). Although autism has been reported among infants with prenatal exposure to thalidomide, cocaine, alcohol, and valproate, most infants prenatally exposed to these and other drugs or chemical agents do not develop autism.

The genetic contribution to the causation/predisposition to autism is considered to be substantial on the basis of high concordance in monozygous twins, a recurrence rate of about 5% among siblings, the uniquely high male:female ratio (about 4:1 in most studies), the co-occurrence of autism with a number of single gene disorders and chromosome aberrations, and the presence of behavioral disturbances among first degree relatives. These considerations aside, no single specific genetic cause has been found to explain more than 1-2% of autism cases, and overall only in 10-20% of autism cases can a cause be determined.

The strongest evidence for a heritable basis of autism comes from twin studies. Overall, these studies show high concordance of autism among monozygous (MZ) twins and low concordance among same sex dizygous (DZ) twins, resulting in greater than ninety percent heritability estimates. Four prominent studies dealing specifically with autistic disorders (narrowly defined to exclude Asperger disorder and Pervasive Developmental Disorder Not Otherwise Specified) report concordance of 36-96% in MZ twins and 0-30% in same-sex DZ twins (Folstein and Rutter 1977, Ritvo et al. 1985, Steffenburg et al. 1989, Bailey et al. 1995).

Chromosomal abnormalities have been found in a number of individuals with autism. These include marker chromosomes, microdeletions and microduplications, rearrangements, and autosomal fragile sites (Schroer et al. 1998, Ullmann et al. 2007, Morrow et al. 2008, Freitag 2007, Sebat et al. 2007, Weiss et al. 2008, Marshall et al. 2008). Taken together, these observations do not suggest a single underlying chromosomal aberration, but rather that a variety of chromosomal changes may disturb brain development and function in a way that leads to autism.

A number of genome-wide screens to identify chromosomal regions linked to autism susceptibility have been reported. However, the study of candidate genes within many of these linkage regions has failed to identify genes that clearly cause or strongly predispose to autism.

Although several X-linked genes have been associated with autism or autistic features in males, X-chromosomal loci have not been implicated in autism by linkage analyses. This may be explained in part by existence of multiple X loci of importance (heterogeneity) or by the uninformative nature of the sib-pairs used in the analysis. Of greater importance is that linkage analysis would not detect epigenetic modifications of gene(s) on the X chromosome.

The recurrence rate in brothers and sisters of affected persons is 3-8%. This recurrence rate is less than expected if all cases were caused by autosomal recessive gene mutations (25%) or autosomal dominant gene mutations (50%). The rate is not unlike that found in conditions considered to have multifactorial causation, such as neural tube defects and cleft lip/palate. Multifactorial causation implies collaboration between multiple genetic factors and environmental influences.

The various chromosomal alterations and gene mutations currently reported in association with autism indicate the genetically heterogeneous nature of autism and taken together account for only a minority (less than 20%) of cases. No laboratory finding has been consistently abnormal, although plasma serotonin levels may be elevated in affected individuals and first-degree relatives. James et al. (2006, 2008) have proposed that metabolic vulnerability to oxidative stress may be an autism susceptibility factor, and Carter (2007) has suggested that the skewed male:female ratio in autism may be explained by sex-specific responses to the neuropeptides, oxytocin and vasopressin.

As the underlying causes of ASDs remain elusive, and though several biochemical markers have been inconsistently associated with autistic traits (e.g., hypersertoninemia, urinary catabolites, and oxidative metabolism markers), there remains a need for a relatively simple laboratory test that can offer a reliable confirmation for the clinical diagnosis of ASDs and/or to provide a route for an efficient screening of individuals with autism. Because of the absence of consistent physical findings in autism and the uncertainty of the diagnosis in the first years of life, a laboratory test that helps diagnose autism, particularly at an early age, would be of great benefit.

SUMMARY

A method for diagnosing autism spectrum disorder is disclosed. The method can include, for instance, deriving a cell sample from a test subject and culturing the cell sample in a culture medium. More specifically, the only energy source for the cells of the cell sample within the medium can include tryptophan, for instance tryptophan alone or a dipeptide containing tryptophan. The method can also include determining the presence or quantity of a marker in the culture medium, wherein the marker is a component of the kynurenine pathway.

BRIEF DESCRIPTION OF THE FIGURES

A full and enabling disclosure of the present disclosure, including the best mode thereof to one skilled in the art, is set forth more particularly in the remainder of the specification, which includes reference to the accompanying figures, in which.

DEFINITIONS

Figure 1:
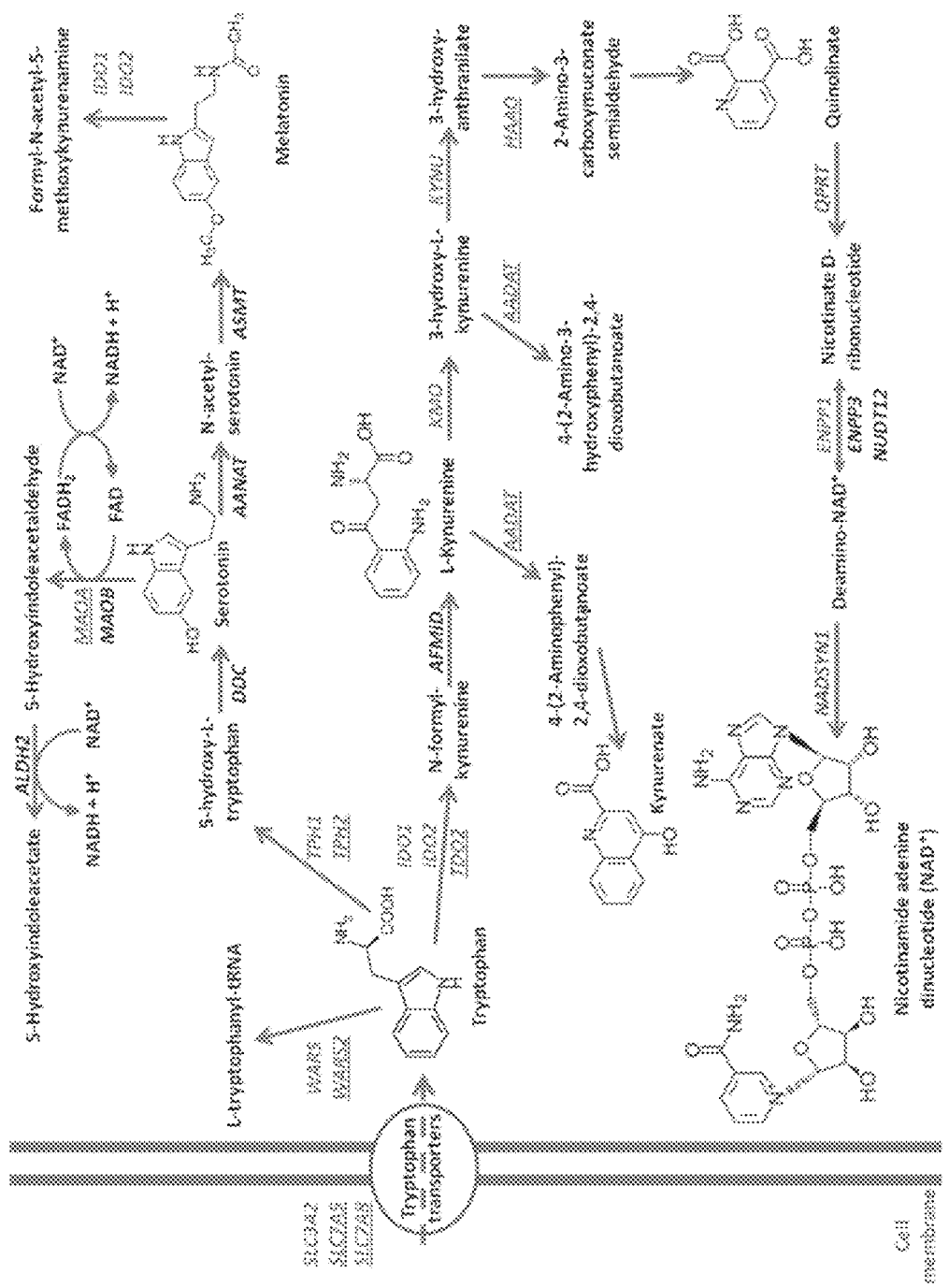
FIG. 1 illustrates the kynurenine pathway.

As used herein, the terms "autism" and "autism spectrum disorders" (ASDs) are used interchangeably to generally describe three of the five developmental disorders described in the Diagnostic and Statistical Manual, IVth Edition (DSM IV-TR): autistic disorder, Asperger disorder, and Pervasive Developmental Disorder Not Otherwise Specified (American Psychiatric Association 2000). The clinical hallmarks of autism include disturbances in three categories of behavior—reciprocal social interactions, verbal and nonverbal communications, and age appropriate activities and interests. Intellectual disabilities coexist in over two-thirds of individuals diagnosed with ASDs but are conspicuously absent in Asperger disorder. The other neurological manifestation of note is seizures, which occur in 20-35% of individuals with autism spectrum disorders.

The physical appearance of individuals with autism is generally unremarkable, characterized by normal facial appearance, musculoskeletal structures, internal organs, and sexual development. Intrauterine and postnatal growth usually follows a normal course. A subgroup of approximately 20% of individuals with autism has macrocephaly, which is usually acquired during the first four years of life. Generalized brain overgrowth and cerebellar hypoplasia have been found in some cases using brain-imaging techniques. Reduced Purkinje cell counts in the cerebellum, reduced neuron size and absence of gliosis have been noted on brain microscopy. Hypotonia and amygdala/limbic system abnormalities also have been noted in affected individuals as have disrupted organization of fronto-temporal lobes and abnormalities in the minicolumns.

As used herein, the term "normal" with regard to the level of tryptophan metabolism generally refers to the average level of production of a tryptophan metabolism marker in individuals not affected by any autism spectrum disorders.

As used herein, the terms "affected" and "affected person" generally refer to a person with features of autism or ASDs as defined by The American Psychiatric Association (2000). While males are more commonly affected with ASDs, both males and females may be affected. Conversely, the terms "non-affected" and "non-affected person" refers to a person without features of ASDs as defined by The American Psychiatric Association (2000).

As used herein the term "marker" generally refers to a compound that can be used to directly or indirectly identify an individual affected with autism. More specifically, markers can include products of the kynurenine pathway for tryptophan metabolism, such as NADH.

The terms "protein," "peptide" and "polypeptide" are used interchangeably herein.

DETAILED DESCRIPTION

Reference now will be made to embodiments of the disclosure, one or more examples of which are set forth below. Each example is provided by way of an explanation of the disclosure, not as a limitation of the disclosure. In fact, it will be apparent to those skilled in the art that various modifications and variations can be made in the disclosure without departing from the scope or spirit of the disclosure. For instance, features illustrated or described as one embodiment can be used on another embodiment to yield still a further embodiment. It is to be understood by one of ordinary skill in the art that the present discussion is a description of exemplary embodiments only, and is not intended as limiting the broader aspects of the present disclosure, which broader aspects are embodied in exemplary constructions.

Disclosed herein are methods for diagnosis of ASDs. More specifically, disclosed methods can utilize a relatively simple laboratory screening method that can be carried out with a cell sample obtained from a test subject. Beneficially, the screening method can be carried out with a test subject of any age, and as such can provide an early diagnosis, which can result in early treatments that can, e.g., improve speech development and social interaction. Methods can also provide pre-symptomatic screening for siblings of affected patients, a delicate issue for many families with an affected relative that have in the past had to wait for the proband to reach approximately 3 years of age to be evaluated.

The disclosed screening methodology has been developed based upon the determination that persons with ASDs can fail to properly metabolize tryptophan. Disclosed methods are thus directed to the determination of an individual's ability to metabolize tryptophan, wherein a determination that a subject does not properly metabolize tryptophan is an indication that the subject may be affected with ASDs. Methods disclosed herein can be utilized as a quick and reliable diagnostic tool for ASDs and have the potential for providing a unifying model for the genetic heterogeneity of ASDs.

Tryptophan is an essential amino acid and is a precursor for the biosynthesis of serotonin. Serotonin has been associated with mood regulation and early regulation of neuronal morphology and circuitry. Tryptophan is metabolized by the kynurenine pathway (FIG. 1), which produces quinolinic acid and kynurenic acid, two critical regulators of neuronal development and synaptogenesis.

Impaired tryptophan metabolism in patients with ASDs can indicate a potential predisposition of cells for mitochondrial dysfunction. Microarray data described in more detail below have revealed that the mitochondrial isoform of tryptophanyl tRNA synthetase (WARS2) was significantly under-expressed in 10 ASDs cell lines (P value=0.0159) as compared to 10 control cell lines, while the cytoplasmic isoform (WARS1) showed no difference in expression levels (P value=0.3550). Considering that the expression of tRNA genes is sensitive to the availability of the corresponding amino acid, it is believed that the tryptophan levels in mitochondria were lower in ASDs patients than controls.

Mitochondrial dysfunction has important consequences in those tissues requiring higher energy levels. In the brain, such dysfunction has an effect on neuronal development and morphology, neurite overgrowth and synaptic plasticity. Mitochondrial activity can be influenced by disruption of the excitatory-inhibitory ratio in synapses. There appears to be a close link between mitochondrial dysfunction and synaptic abnormalities, which are considered one of the main pathogenic events associated with ASDs. Also, some of the pathways involved in regulation of synaptic protein expression are also involved in the expression of protein destined for the mitochondria.

Although roughly 99% of the dietary tryptophan intake is metabolized via the kynurenine pathway, this amino acid is also the main precursor for both serotonin and melatonin. Melatonin plays a critical role in the regulation of circadian rhythm, and anomalies of this rhythm have been associated with some of the symptoms in the autistic spectrum, like seizures or sleep disorders. Serotonin is a neurotransmitter involved in multiple aspects of brain functions, ranging from the regulation of mood to the control of appetite and social interactions and its production has been reported as deficient in ASDs brains. Tryptophan levels have been demonstrated to directly influence central nervous system serotonin levels and behavior, and altered tryptophan transport has been described in fibroblasts from boys with attention deficit/hyperactivity disorder (ADHD).

Serotonin also plays a critical role in regulating neuronal morphology and circuitry and recent work has shown that placental cells are able to synthesize serotonin from tryptophan provided by the maternal blood. This exogenous source of serotonin is important in the neurodevelopment of the forebrain in the first month of gestation, because the fetal source (the hindbrain, which is the future serotonergic system) is not sufficient at this stage. Disrupted organization of the fronto-temporal lobes is one of the most consistent neuroanatomical findings in ASDs patients, and lower expression levels of genes involved in synapses, neurotransmitter transport and neuron projection have been detected in frontal and temporal lobes of ASDs brains. At the cellular level, such disrupted organization is reflected by abnormalities in the minicolumns, the basic functional units of the cortex, which have been reported in ASDs brains to be narrower, increased in number per cortical area and with reduction of neuropil space, caused by the smaller size of the peripheral interneurons.

While not wishing to be bound to any particular theory, it is believed that decreased tryptophan metabolism in patients with ASDs may alter metabolic pathways involved in the regulation of the early stages of brain development (first month of gestation), mitochondrial homeostasis and immune system activity. Microglial cells are considered to be responsible for keeping the proper balance between quinolinic and kynurenic acid, since they are able to secrete both compounds. The expression of quinolinic and kynurenic acid is strongly influenced by activity of the immune system. Particularly, nitric oxide (NO) plays a critical role in the interaction between inflammation and neuronal circuits and causes mitochondrial dysfunction. Significantly, elevated NO levels have been reported in ASD patients. Disruption of such metabolic pathways can primarily be caused either by insufficient serotonin production by placental cells, by mitochondrial dysfunction and/or by impaired balance between quinolinic and kynurenic acid in fetal cells. The combined effects of these events could lead to abnormal organization of neurons (minicolumnopathy), particularly in specific brain regions (fronto-temporal lobes, limbic system), resulting in an imbalance between the short and long term circuitry that has been considered to be one of the fundamentals of autism neuropathology. Decreased tryptophan metabolism in cells from patients with ASDs may provide a unifying model that could help in understanding the genetic heterogeneity of ASDs.

Methods for determining the ability of a subject to properly metabolize tryptophan can include obtaining a cell culture from the subject. The cell culture is then developed under conditions in which the metabolic energy source for the cells is either tryptophan or an oligopeptide that includes tryptophan. Following a development period, the cell culture is examined to determine the ability of the test subject to metabolize tryptophan through extraction and quantification of a marker that signifies proper metabolism of tryptophan through the kynurenine pathway.

Specific cell types that can be examined in a method are not particularly limited, and the cells can generally be of any type that metabolizes tryptophan. For example, fibroblasts, adipocytes, induced pluripotent stem cells, neuroblasts, leukocytes, e.g., lymphocytes or granulocytes, can be examined. The cells to be examined can be differentiated or undifferentiated cells. For instance, lymphocytes or leukocytes from a test subject can be examined. A cell line developed from a test subject, for instance a lymphoblastoid cell line developed from a test subject can alternatively be utilized in a process.

The cells can be obtained according to any suitable process as is known in the art. In one embodiment, cells obtained directly from a subject may be examined. In another embodiment, a cell culture obtained directly from a subject, and a cell line developed from that original culture, with the cells to be tested those of that developed cell line.

According to one embodiment, a blood sample can be obtained from a test subject and leukocytes can be isolated from the blood sample. The isolated leukocytes can then be utilized to determine the test subject's ability to metabolize tryptophan. The number of cells required for a testing protocol is not particularly limited, and the sample size can be relatively small and provide excellent results. In general, a cell sample of up to about 300,000 cells, or up to about 200,000 cells will be adequate. When considering a leukocyte sample derived from a blood sample, a blood sample can be less than about 1 mL, less than about 0.5 mL, or less than about 0.1 mL, for instance between about 0.03 and about 0.075 mL in one embodiment.

The cells can be cultured in an environment that limits the energy source for the cells. More specifically, the media can be a starvation media in which the energy source provided for metabolism of the cells is isolated tryptophan (i.e., the tryptophan amino acid that is not a tryptophan residue portion of a peptide), a tryptophan dipeptide, or a combination thereof. In one embodiment, a longer peptide comprising tryptophan may be utilized, for instance up to about 5 amino acid residues. However, depending on the specific make-up of the longer peptide, increasing the length of the peptidic energy source beyond the dipeptide can lead to a loss of resolution in the results of the cell culture with regard to tryptophan metabolism. For example, when utilizing a longer peptide as an energy source, the dipeptidase enzymes can cut the peptide into single amino acids or dipeptides, some of which could include amino acid residues other than tryptophan. This could lead to less specificity with regard to the ability of the cells to properly metabolize tryptophan.

When considering a dipeptide as the energy source, any dipeptide of tryptophan can be utilized, i.e., the tryptophan can be the first position, the second position, or both on a dipeptide, and the other amino acid of the dipeptide can be any amino acid. In addition, combinations of dipeptides can be utilized.

The period of time during which the cell culture is maintained on starvation conditions with the tryptophan-based energy source being the only energy source provided can be long enough to ensure results, but not too long, to avoid cell death. More specifically, the culture time should be of a period so as to determine the ability of the cells to metabolize the limited energy source with high accuracy. In general, a culture period can be greater than about 12 hours. For instance, the cells can be cultured on the limited energy source for a period of time between about 12 hours and about 48 hours, for example about 24 hours.

Following culturing, the cell culture can be examined for the presence or amount of one or more markers that indicate tryptophan metabolism, or a lack thereof. More specifically, the marker can be a component of the kynurenine pathway (FIG. 1). The kynurenine pathway has two major final products: quinolinic acid that is metabolized to nicotinamide and nicotinamide adenine dinucleotide (NAD), and kynurenic acid. In one embodiment, the marker can be NAD. Any form of NADH can be utilized as a marker, including $NAD^+$, the reduced form of the dinucleotide, NADH, the phosphorylated form of the dinucleotide, $NADP^+$, and/or the reduced phosphorylated compound NADPH.

The inability to properly metabolize tryptophan can be indicated by a decrease or lack of the presence of the biomarker in the cell culture following an incubation period as compared to a control value for non-affected individuals. For instance, a significant difference in the level of the biomarker in one or more cell cultures of a subject as compared to that of a control value as determined for non-affected individuals can be an indication of an inability to properly metabolize tryptophan. For example, one or more different tryptophan-based energy sources can be utilized in separate cell cultures, all containing cells obtained from or derived from a single test subject, and a consistent (e.g. present in about 90% or more of the separate cell cultures) and statistically significant (e.g., P value less than about 0.05) difference in the level of the biomarker for the test subject as compared to a control value can be an indication of an inability to properly metabolize tryptophan and as such, an indication of autism in the test subject.

Any method of detecting the presence or amount of the marker in the cell culture may be utilized, including, but not limited to, Western blot analysis, 2-D gel electrophoresis, mass spectrometry, heterogeneous assays, homogeneous assays, wet chemistry assays, dry chemistry assays, metabolic assays, and so forth. In one embodiment, an ELISA type assay as is generally known in the art can be utilized. In another embodiment, a redox-based assay such as the microarray system available from Biolog, Inc. (Hayward, Calif.) can be utilized in determining the presence or quantity of the marker in the cell culture.

The level of a marker can generally be detected through utilization of a detectable label. In general, any suitable detectable label can be utilized. For example, a detectable label, e.g., a fluorescent label, a phosphorescent label, a radioisotope, and the like, can be bound to a molecule that can bind to a marker. In one embodiment, a detectable label can directly or indirectly specifically bind to a marker. For example, a detectably organic compound can specifically bind to a marker so as to function as a probe for that marker.

Any substance capable of producing a signal that is detectable visually or by an instrumental device may be used as the detectable label. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth.

It is generally desired to modify the detectable label in some manner so that it is more readily able to bind to the marker. In such instances, the detectable label may be modified with certain specific binding members that are adhered thereto to form conjugated probes. It is normally desired that the detectable label is conjugated with a component that can specifically bind to the marker, e.g., NADH, either directly or indirectly.

Some examples of suitable immunoreactive specific binding members that may be used include, but are not limited to, antigens, haptens, aptamers, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Furthermore, specific binding members may include compounds that are analogs of the original specific binding member. For example, a derivative or fragment of another specific binding member may be used so long as it has at least one epitope in common with the original specific binding member.

The specific binding members may generally be attached to the detectable label to form a conjugated probe using any of a variety of well-known techniques. For instance, covalent attachment of the specific binding members to the detectable label may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished.

A probe can be fixed to a substrate through either covalent or non-covalent association. In general, however, a probe can be bound to a substrate and washed to some significant degree of stringency (e.g. standard saline citrate, pH 7.4) without a substantial fraction of the probe dissociating from the substrate. For example, probes can be printed onto a substrate using photolithography techniques using pre-made masks, dynamic micromirror devices, ink-jet printing, or electrochemical processes.

Optionally, a probe can be chemically bound to a substrate. For instance, a probe can be bound to a substrate via, for example, amine, carboxylic acid, hydroxy, aldehyde, thiol, or ester functionality on a prepared surface. For example, a substrate surface may be aminated through contact with an amine-containing compound such as 3-aminopropyltriethoxy silane in order to increase the amine functionality of the surface and bind a probe to the surface via the added amine functionality. A probe may be bound to a substrate via a streptavidin/biotin binding system, an antibody/hapten bridging system, and the like.

It should be understood, however, that the binding of a probe to a substrate is not a requirement of disclosed systems, and in other systems, a probe can be in solution such that a marker/probe complex can be formed in solution.

Following suitable contact of the cell culture with the probe, for instance following an incubation period, the presence or amount of the marker in the sample may be determined, either visually or with instrumentation. For example, the intensity of the color of the incubated sample may be measured to quantitatively or semi-quantitatively determine the level of NADH present in the test sample. The intensity of the color is typically directly proportional to marker concentration. The intensity of the detection signal produced in the sample may also be compared to a predetermined detection curve developed for a plurality of known marker concentrations. To determine the quantity of the marker in an unknown test sample, the signal may simply be converted to marker concentration according to the detection curve.

Reference now will be made to embodiments of the disclosure, examples of which are set forth below. Each example is provided by way of an explanation of the disclosure, not as a limitation of the disclosure. In fact, it will be apparent to those skilled in the art that various modifications and variations can be made in the disclosure without departing from the scope or spirit of the disclosure. For instance, features illustrated or described as one embodiment can be used on another embodiment to yield still a further embodiment.

The examples present the results of the analysis of the metabolic profile of lymphoblastoid cell lines from patients with ASDs and normal individuals, utilizing the Phenotype MicroArray methodology developed by Biolog (Hayward, Calif.). An analysis of the metabolic profile of lymphoblastoid cell lines from patients with ASDs and controls was undertaken. Overall, it was found that 104/106 (98.1%) of patients showed a statistically significant difference as compared to controls in the generation of NADH when tryptophan was the primary metabolic energy source available, reflecting decreased tryptophan metabolism.

Example 1

20,000 lymphoblastoid cells were used per well. The cells were incubated under carbon starvation conditions for 48 hours at 37° C. at 5% of $CO_2$, using the modified Biolog IF-M1 medium. The medium included 100 ml of Biolog IF-M1 (provided with the test kit), 1.1 ml of 100× Penicillin/Streptomycin solution, 0.16 ml of 200 mM Glutamine (final concentration 0.3 mM), and 5.3 ml of Fetal Bovine Serum (final concentration 5%). Glutamine was included in the medium at a basal level to ensure cell division, but was provided in an amount insufficient to allow any further metabolic reactions. During this time the primary metabolic energy source the cells had was the tryptophan source provided in the well. After this first incubation, BiologRedox Dye Mix MB was added (10 μl/well) and the plates were incubated under the same conditions for 24 hours. The dye reacted in a redox reaction and showed a change in color, from yellow to purple, according to the amount of NADH generated in the presence of the energy source.

At the end of the 24-hour incubation in the presence of the dye, the plates were analyzed at absorbances of 590 and 750 nm utilizing a microplate reader. The first value ($A_{590}$) indicates the highest absorbance peak of the redox dye and the second value ($A_{750}$) gives a measure of the background noise. The relative absorbance ($A_{590-750}$) was calculated per well and is provided in the results below as a measure of NADH production (Table 1).

For Biolog data, the absorbance readings were transformed into logarithmic scale. Two primary statistical approaches were taken. First, it was assumed that as a group, patients with autism contain a shared Biolog profile. The test was to look for the wells in the autistic samples that are significantly different from the controls. The statistical program, Significance Analysis of Microarray (SAM), was utilized, which implements a modified t-test by assigning a score to each observation on the basis of change and utilizes permutations to estimate the percentage of observations identified by chance using false discovery rate (FDR). FDR maintains a balance between the number of false positives and true positives and is equivalent to the family-wise error but with a gain in power. Second, it was also assumed that there exists individual variation in metabolic profile that is unique to each and every autistic proband. To dissect the individuality and the heterogeneity in the data, the non-parametric Wilcoxon one-sample test was utilized, which tests whether a single specimen belongs to a given population. The Wilcoxon one-sample test has the advantages of being free of the assumption of normality and being insensitive to outliers. The test was performed using the R-language.

For the Agilent expression arrays, data normalization and statistical analysis were performed according to standard protocol.

Plates with carbon energy sources (plate PM-M1) and amino acids, both alone and as dipeptides (plates PM-M2 to M4) were utilized. Each well contained a single chemical as the primary metabolic energy source. The assay, as carried out, measures the production of NADH after 72 hours in the presence of each substrate.

Initially, 10 cell lines were tested from patients with non-syndromal autistic disorder and known genetic alterations (Table 1, Column A, substrates that include tryptophan are shown in bold font) and 10 random controls which were age matched and from the same geographic area (Table 1, Control). The patients labeled with autistic disorder were diagnosed following evaluation with the Autism Diagnostic Interview-Revised (ADI-R) questionnaire and according to the DSM IV-Revised criteria. Genetic tests excluded major chromosomal abnormalities, Fragile X syndrome, Rett syndrome, and abnormalities in plasma amino acid level. Four patients showed an abnormal level of genomic methylation as measured by a NimbleGen methylation assay, 3 had SHANK3 mutations, 2 had NLGN4 mutations, and one had a balanced translocation involving chromosomes 14 and 15. Two of these patients were monozygotic male twins and showed abnormal methylation.

In all 10 ASDs patients, 25/26 (96.1%) wells with tryptophan showed a significantly lower level of NADH generation (P value<0.05) (Table 1, Column A). This finding was independent of whether tryptophan was alone in the well or in the first or second position of a dipeptide. No other substrate consistently exhibited statistically significant differences between patients and controls.

Preliminary expression analysis was performed using Agilent Whole Human Genome Oligo Microarrays of the RNA extracted from the 10 patient cell lines. The analysis revealed that two genes, SLC7A5 and SLC7A8, coding for tryptophan receptor subunits, expressed in both blood and brain were found to be under-expressed (P value=0.00627 and 0.04067, respectively). Significantly reduced expression levels of several enzymes involved in the tryptophan metabolism, particularly AADAT (P value=0.0022), HAAO (P value=0.0158), and MAOA (P value=0.0027) were also detected. In addition, it was found that the mitochondrial isoform of tryptophanyl tRNA synthetase (WARS2) was significantly underexpressed in the 10 ASDs cell lines (P value=0.0159) as compared to 10 control cell lines, while the cytoplasmic isoform (WARS1) showed no significant difference in expression levels (P value=0.3550). The decreased level of NADH generation in the presence of tryptophan may reflect lower utilization of tryptophan by the lymphoblasts which results in down-regulation of the down-stream metabolic reactions leading to lower NADH production.

It is noteworthy that tryptophan hydroxylase is the rate-limiting enzyme in the biosynthesis of serotonin and the gene coding the isoform 2 of this enzyme (TPH2) was under-expressed in this microarray analysis of lymphoblastoid cells from these 10 ASDs patients as compared to that for the controls (P value=0.0166). In the human brain, both isoforms, TPH1 and TPH2, are ubiquitously expressed with some particular region-specific differences and TPH2 expression is significantly higher in the raphe nuclei, the core of serotonergic system. Thus, lower expression levels of TPH2 in white cells might reflect abnormal serotonergic activity in the raphe nuclei.

Seven other cell lines from patients with syndromal autism were also tested: 4 cases with Fragile X (Table 1, Column B), autistic features and full methylation at the FRAXA locus; 2 cases with Rett syndrome and MECP2 mutations (Table 1, Column C); and 1 case with a ZNF711 mutation, X-linked intellectual disability and clinical findings consistent with ASDs (Table 1, Column D). All of these patients exhibited a lower generation of NADH in the presence of tryptophan compared to normal controls (Table 1).

TABLE 1

| Substrate | Controls (Average) | A (Average) | B (Average) | C (Average) | D (Average) | P value |
|---|---|---|---|---|---|---|
| Glycogen | 1.489 | 1.164 | 1.161 | 0.911 | 1.402 | 0.026949 |
| L-Lactic Acid (DL) | 0.479 | 0.695 | 0.769 | 0.556 | 0.657 | 0.006211 |
| Succinamic Acid | 1.626 | 1.298 | 1.422 | 0.812 | 1.651 | 0.023753 |
| Mono Methyl Succinate | 1.884 | 1.475 | 1.671 | 0.992 | 1.819 | 0.011704 |
| b-Hydroxy-Butyric Acid | 0.359 | 0.529 | 0.557 | 0.379 | 0.412 | 0.023910 |
| Hexanoic Acid | 0.338 | 0.489 | 0.554 | 0.415 | 0.390 | 0.011992 |
| Tween 20 | 0.105 | 0.072 | 0.075 | 0.136 | 0.085 | 0.031950 |
| L-Tryptophan | 0.631 | 0.365 | 0.375 | 0.241 | 0.377 | 0.001461 |
| Ala-Arg | 0.194 | 0.273 | 0.314 | 0.222 | 0.211 | 0.018475 |
| Ala-Trp | 0.472 | 0.292 | 0.298 | 0.203 | 0.299 | 0.001675 |
| Arg-Trp | 0.357 | 0.235 | 0.238 | 0.165 | 0.232 | 0.001373 |
| Asp-Trp | 0.449 | 0.264 | 0.314 | 0.166 | 0.242 | 0.001115 |
| Glu-Trp | 0.532 | 0.329 | 0.342 | 0.178 | 0.330 | 0.000942 |
| Gly-Trp | 0.462 | 0.317 | 0.297 | 0.184 | 0.299 | 0.006416 |
| Gly-Tyr | 0.277 | 0.201 | 0.231 | 0.146 | 0.189 | 0.015515 |
| His-Trp | 0.379 | 0.247 | 0.254 | 0.187 | 0.249 | 0.004921 |
| His-Tyr | 0.238 | 0.171 | 0.241 | 0.115 | 0.161 | 0.031716 |
| Ile-Gln | 1.021 | 0.728 | 0.979 | 0.904 | 0.611 | 0.029556 |
| Ile-Trp | 0.538 | 0.342 | 0.397 | 0.278 | 0.324 | 0.006989 |
| Ile-Tyr | 0.331 | 0.212 | 0.313 | 0.216 | 0.209 | 0.018489 |
| Leu-Phe | 0.190 | 0.241 | 0.371 | 0.338 | 0.189 | 0.039625 |
| Leu-Trp | 0.498 | 0.334 | 0.371 | 0.372 | 0.320 | 0.002536 |
| Met-Trp | 0.528 | 0.355 | 0.359 | 0.248 | 0.348 | 0.001670 |
| Met-Tyr | 0.310 | 0.225 | 0.275 | 0.168 | 0.215 | 0.021180 |
| Phe-Trp | 0.395 | 0.291 | 0.337 | 0.203 | 0.288 | 0.000191 |
| Pro-Trp | 0.500 | 0.406 | 0.367 | 0.311 | 0.337 | 0.021670 |
| Ser-Tyr | 0.301 | 0.214 | 0.266 | 0.185 | 0.212 | 0.013745 |
| Trp-Ala | 0.486 | 0.324 | 0.321 | 0.223 | 0.309 | 0.001209 |
| Trp-Arg | 0.402 | 0.241 | 0.290 | 0.158 | 0.231 | 0.000173 |
| Trp-Asp | 0.412 | 0.269 | 0.318 | 0.141 | 0.225 | 0.000740 |
| Trp-Glu | 0.494 | 0.288 | 0.352 | 0.162 | 0.255 | 0.000132 |
| Trp-Gly | 0.472 | 0.285 | 0.317 | 0.190 | 0.268 | 0.000299 |
| Trp-Leu | 0.447 | 0.325 | 0.309 | 0.212 | 0.314 | 0.001800 |
| Trp-Lys | 0.399 | 0.310 | 0.276 | 0.163 | 0.279 | 0.014358 |
| Trp-Phe | 0.420 | 0.334 | 0.312 | 0.231 | 0.295 | 0.000590 |
| Trp-Ser | 0.501 | 0.304 | 0.297 | 0.236 | 0.291 | 0.004266 |
| Trp-Trp | 0.505 | 0.332 | 0.320 | 0.219 | 0.341 | 0.000153 |
| Trp-Tyr | 0.472 | 0.305 | 0.295 | 0.179 | 0.287 | 0.001164 |
| Trp-Val | 0.481 | 0.304 | 0.344 | 0.195 | 0.310 | 0.003150 |
| Tyr-Ala | 0.314 | 0.210 | 0.270 | 0.157 | 0.200 | 0.036694 |
| Tyr-Gly | 0.287 | 0.194 | 0.244 | 0.088 | 0.176 | 0.005801 |
| Tyr-Ile | 0.347 | 0.230 | 0.295 | 0.155 | 0.200 | 0.019385 |
| Tyr-Phe | 0.252 | 0.200 | 0.239 | 0.131 | 0.145 | 0.027475 |
| Tyr-Trp | 0.336 | 0.253 | 0.278 | 0.157 | 0.231 | 0.002382 |
| Tyr-Tyr | 0.328 | 0.233 | 0.225 | 0.124 | 0.185 | 0.003382 |
| Tyr-Val | 0.293 | 0.210 | 0.242 | 0.116 | 0.154 | 0.014950 |
| Val-Gln | 0.731 | 0.499 | 0.615 | 0.543 | 0.380 | 0.022287 |
| Val-Tyr | 0.303 | 0.229 | 0.273 | 0.138 | 0.187 | 0.024195 |

To evaluate the specificity of the protocol, cell lines from patients with a syndromal condition which did not present with features consistent with ASDs were also examined according to the described procedure. Two cell lines from patients with Angelman syndrome (a condition often considered in a differential diagnosis with Rett syndrome) who did not meet criteria for ASDs were analyzed, and the tryptophan-NADH data were similar to controls (data not shown). A patient with a ZNF711 mutation who did not exhibit ASDs features was also tested and there was no detection of any differences in the generation of NADH for tryptophan containing wells as compared to controls (data not shown). Next, 35 patients with intellectual disability carrying pathogenic mutations in ID-associated genes were tested as well as 10 patients with schizophrenia and none of these individuals exhibited any significant difference from controls in the generation of NADH in the presence of tryptophan (data not shown). Thus, overall, these data suggested that lower levels of NADH generation in the presence of tryptophan was 1) a feature common to the 17 ASDs patient cell lines tested, independent of whether the autistic traits were the sole clinical findings in the patients or whether they were accompanied by other symptoms in a syndromal condition, 2) was not observed in patients with similar conditions but without features consistent with ASDs and 3) was not observed in other neurocognitive conditions.

Example 2

20 patients with autistic disorders, according to the DSM IV-Revised criteria were tested as described in Example 1 along with 20 controls, including 10 controls tested in Example 1, utilizing only the PM-M4 plate, which contained 12 wells with tryptophan as the first amino acid of the dipeptide provided as the primary metabolic energy source. The PM-M4 plate energy source contents are described in Table 2, below.

TABLE 2

| Well No. | Energy Source | Well No. | Energy Source | Well No. | Energy Source | Well No. | Energy Source |
| --- | --- | --- | --- | --- | --- | --- | --- |
| A01 | Neg. | C01 | Pro-Pro | E01 | Thr-Gly | G01 | Tyr-Leu |
| A02 | Neg. | C02 | Pro-Ser | E02 | Thr-Leu | G02 | Tyr-Lys |
| A03 | Neg. | C03 | Pro-Trp | E03 | Thr-Met | G03 | Tyr-Phe |
| A04 | Phe-Gly | C04 | Pro-Tyr | E04 | Thr-Phe | G04 | Tyr-Trp |
| A05 | Phe-Ile | C05 | Pro-Val | E05 | Thr-Pro | G05 | Tyr-Tyr |
| A06 | Phe-Met | C06 | Ser-Ala | E06 | Thr-Ser | G06 | Tyr-Val |
| A07 | Phe-Phe | C07 | Ser-Asn | E07 | Trp-Ala | G07 | Val-Ala |
| A08 | Phe-Pro | C08 | Ser-Asp | E08 | Trp-Arg | G08 | Val-Arg |
| A09 | Phe-Ser | C09 | Ser-Glu | E09 | Trp-Asp | G09 | Val-Asn |
| A10 | Phe-Trp | C10 | Ser-Gln | E10 | Trp-Glu | G10 | Val-Asp |
| A11 | Phe-Tyr | C11 | Ser-Gly | E11 | Trp-Gly | G11 | Val-Glu |
| A12 | Phe-Val | C12 | Ser-His | E12 | Trp-Leu | G12 | Val-Gln |
| B01 | Pro-Ala | D01 | Ser-Leu | F01 | Try-Lys | H01 | Val-Gly |
| B02 | Pro-Arg | D02 | Ser-Met | F02 | Trp-Phe | H02 | Val-His |
| B03 | Pro-Asn | D03 | Ser-Pro | F03 | Trp-Ser | H03 | Val-Ile |
| B04 | Pro-Asp | D04 | Ser-Pro | F04 | Trp-Trp | H04 | Val-Leu |
| B05 | Pro-Glu | D05 | Ser-Ser | F05 | Trp-Tyr | H05 | Val-Lys |
| B06 | Pro-Gln | D06 | Ser-Tyr | F06 | Trp-Val | H06 | Val-Met |
| B07 | Pro-Gly | D07 | Ser-Val | F07 | Tyr-Ala | H07 | Val-Phe |
| B08 | Pro-Hyp | D08 | Thr-Ala | F08 | Tyr-Gln | H08 | Val-Pro |
| B09 | Pro-Ile | D09 | Thr-Arg | F09 | Tyr-Glu | H09 | Val-Ser |
| B10 | Pro-Leu | D10 | Thr-Asp | F10 | Tyr-Gly | H10 | Val-Tyr |
| B11 | Pro-Lys | D11 | Thr-Glu | F11 | Tyr-His | H11 | Val-Val |
| B12 | Pro-Phe | D12 | Thr-Gln | F12 | Tyr-Ile | H12 | D-(+)-glucose |

Figure 2:
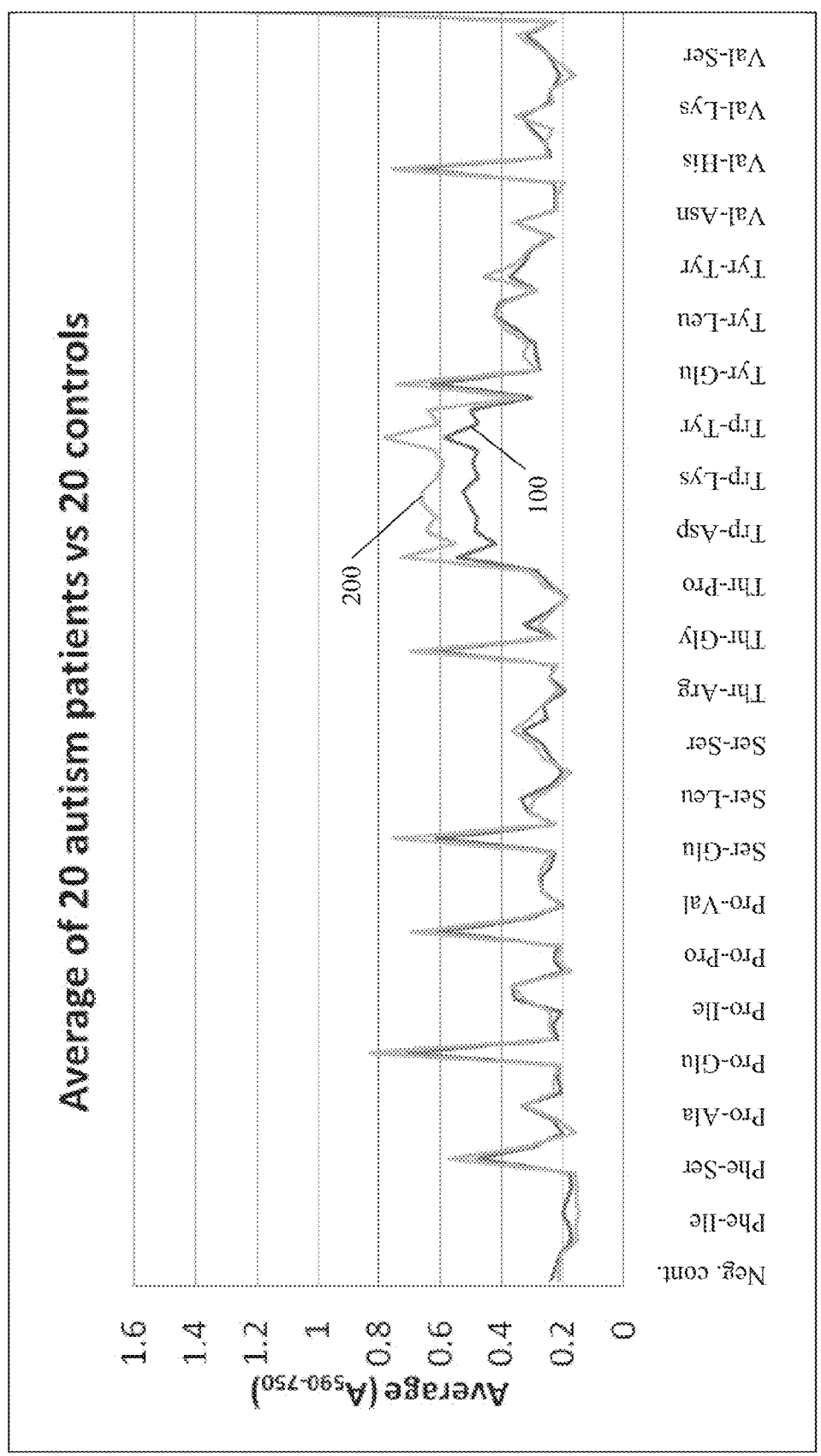
FIG. 2 represents data showing the degree of nicotinamide adenine dinucleotide (NADH) generation by 20 patients diagnosed with ASDs and 20 controls. The wells between E7 and F6 contained tryptophan dipeptides as the sole energy source and show the significant differences between the autism patients and the controls.

The findings confirmed the lower production of NADH in the patients 100 as compared to controls 200 (FIG. 2, showing the results for each well, selected well contents provided on the axis of the graph). The difference was statistically significant when the averages of the two cohorts were compared as well as when each patient versus the control average was compared. In the first analysis (FIG. 2) the averages of the 12 wells including tryptophan in the dipeptide energy source between the two groups showed statistically significant differences (P value=0.018). After comparison of each patient versus control average, only 2 out of 20 patients did not show differences. Overall, including the 17 cases described in Example 1, significant differences in NADH generation in 35/37 ASDs patients (94.6%) were detected.

Example 3

Samples from 19 ASDs patients (18 with autistic disorder and 1 with Pervasive Developmental Disorder Not Otherwise Specified, PDD-NOS, according to the DSM IV-Revised criteria) were analyzed along with samples from 20 controls (different from the controls used in Example 1 and Example 2). The PM-M4 plates of the Biolog, Inc. system were used including the 12 wells containing tryptophan. The experiment followed the same protocol described in Example 1. The results confirmed a significantly lower NADH generation from tryptophan in the 19 ASDs patients, both in comparison to the 20 controls or when compared to the average of all the 40 controls. Therefore a significantly reduced NADH production was observed in 54/56 ASDs patients (96.4%) over four experiments. Testing of the subsequent groups of 20 and 19 patients identified the following genetic variants: 7 patients carried the MET rs1858830 C/C polymorphism, 5 showed chromosomal rearrangements upon the array-CGH analysis, 2 had a mutation in the ZBTB20 gene, and 1 had a mutation in the OCRL1 gene.

Example 4

In order to determine if some of the substrates were better at distinguishing patients from controls, multiple machine learning methods were employed. Because each method contains its own bias, a 'voting' strategy was adopted to determine which substrate was selected by the majority of the algorithms. Ten selection methods were utilized (CfsSubsetEval, ChiSquared, FilteredAttribute, FilteredSubset, GainRatioAttribute, InfoGainAttribute OneRAttribute, ReliefFAttribute, SVMAttribute, SymmetricalUncertAttribute) in the Weka package, which is open source software issued under the GNU General Public License.

5 dipeptides were determined to be the most informative. The five wells were found to be, in order of informative power: tryptophan-glycine (Trp-Gly), tryptophan-lysine (Trp-Lys), tryptophan-alanine (Trp-Ala), tryptophan-arginine (Trp-Arg), and tryptophan-leucine (Trp-Leu).

Figure 3:
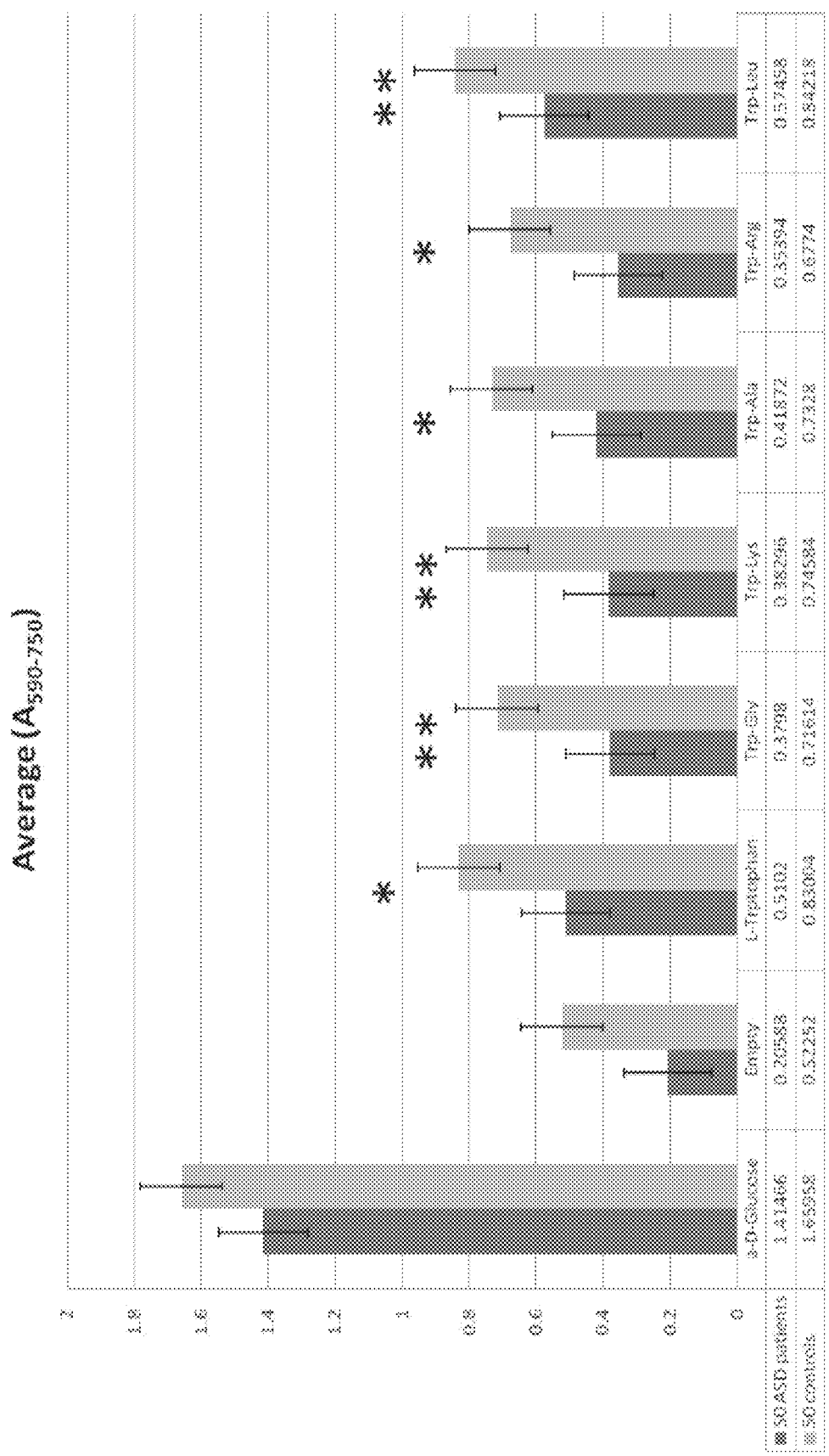
FIG. 3 represents data showing the NADH average generation by 50 patients diagnosed with ASDs and 50 controls. (* indicates P value less than 0.001; and ** indicates P value less than 0.0001.)

Utilizing these results, a customized 96-well plate was designed with 12 columns of 8 wells. These customized plates were used to test lymphoblastoid cell lines from new, unrelated cohorts of 50 ASDs patients and 50 controls. The test was performed as described in Example 1. This experiment replicated the significant differences found previously in the production of NADH in the presence of tryptophan (Bonferroni correction, P values=0.0001, L-Trp; 0.00002, Trp-Gly; 0.00006, Trp-Lys; 0.0005, Trp-Ala; 0.0002, Trp-Arg; 0.00003, Trp-Leu; see FIG. 3).

Thus, when considering all of Examples 1-4 overall, 104/106 (98.1%) lymphoblastoid cell lines from ASDs patients exhibited statistically significant metabolic differences in the level of NADH generated when compared to 90 age-matched controls when tryptophan, either alone or as a dipeptide, was the sole energy source.

Results obtained correlated with the behavioral traits associated with either syndromal or non-syndromal autism, independent of the genetic background of the individual. The low level of NADH generation in the presence of tryptophan was not observed in cell lines from patients with ID or schizophrenia, or affected by conditions showing several similarities with syndromal autism except for the behavioral traits. Tryptophan is directly involved in NADH synthesis, through the kynurenine-quinolinc acid pathway, so these findings could be interpreted as consequences of a disruption of the utilization of tryptophan either as energy source or as structural precursor, or both.

Example 5

A blood sample was obtained from 12 ASDs patients and 12 normal individuals ("controls"). Each sample was examined in duplicate for low levels of NADH production in presence of tryptophan in leukocytes, as had been previously observed in lymphoblasts, with the results averaged as shown below in Table 3. The testing was then carried out as described in Example 1.

Figure 4:
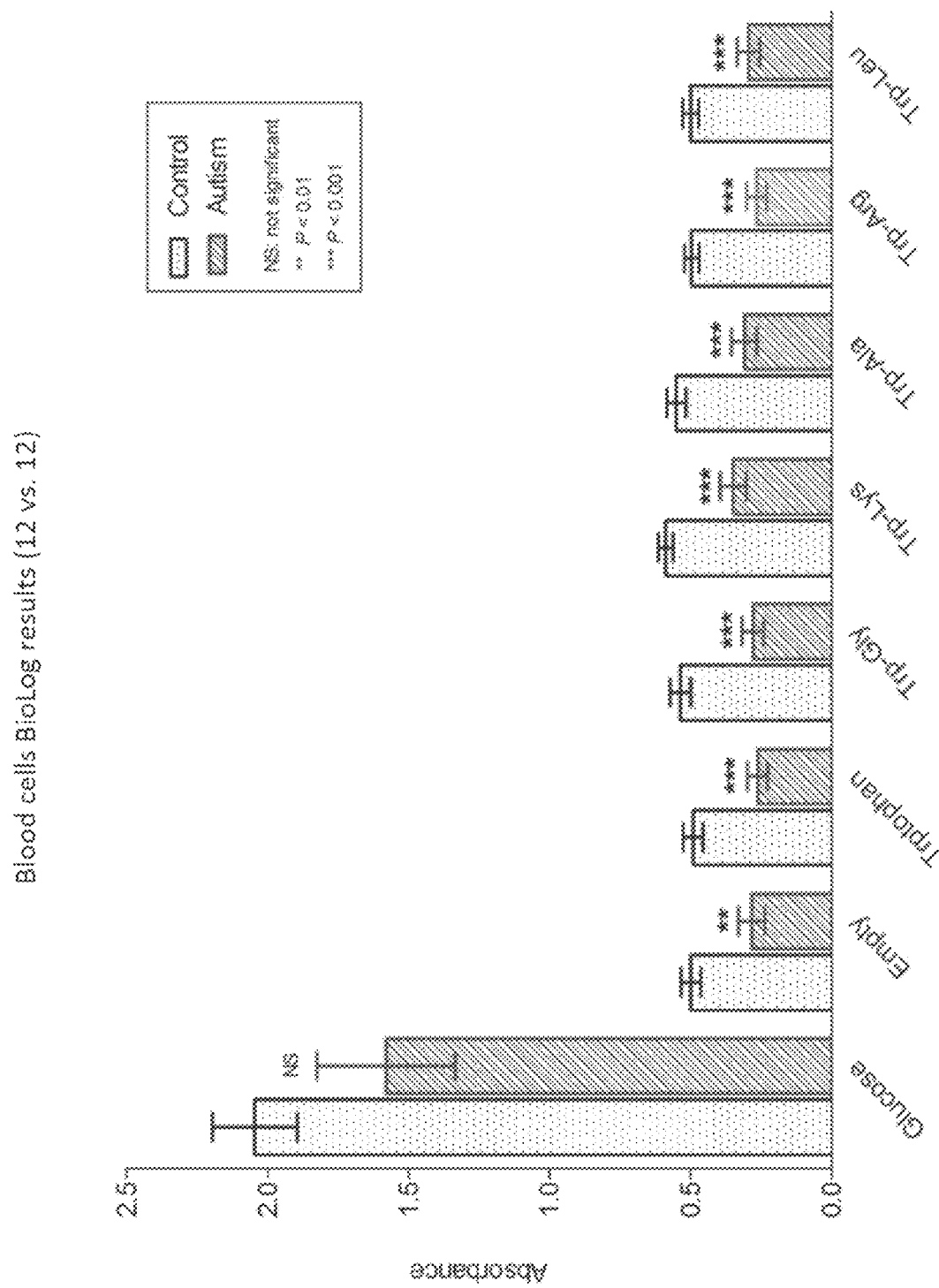
FIG. 4 represents data showing the NADH average generation by 12 patients diagnosed with ASDs and 12 controls.

As shown in FIG. 4 (and its underlying data in Tables 3 and 4), the findings confirmed the lower production of NADH in the patients as compared to controls. The difference was statistically significant when the averages of the two cohorts were compared as well as when each patient versus the control average was compared. Table 3 and 4 shows the results of this analysis:

TABLE 3

| Substrate | ASD1 | ASD2 | ASD3 | ASD4 | ASD5 | ASD6 | ASD7 | ASD8 | ASD9 | ASD10 | ASD11 | ASD12 |
|---|---|---|---|---|---|---|---|---|---|---|---|---|
| a-D-Glucose | 0.756 | 0.952 | 0.544 | 2.630 | 1.604 | 2.296 | 1.016 | 1.100 | 0.861 | 2.717 | 2.913 | 1.568 |
| Empty | 0.035 | 0.559 | 0.372 | 0.264 | 0.263 | 0.426 | 0.214 | 0.284 | 0.088 | 0.303 | 0.487 | 0.108 |
| L-Trp | 0.061 | 0.439 | 0.217 | 0.321 | 0.241 | 0.351 | 0.209 | 0.268 | 0.077 | 0.323 | 0.453 | 0.192 |
| Trp-Gly | 0.046 | 0.418 | 0.253 | 0.379 | 0.259 | 0.345 | 0.215 | 0.293 | 0.086 | 0.350 | 0.524 | 0.186 |
| Trp-Lys | 0.051 | 0.561 | 0.376 | 0.392 | 0.288 | 0.446 | 0.126 | 0.323 | 0.393 | 0.359 | 0.598 | 0.262 |
| Trp-Ala | 0.056 | 0.556 | 0.308 | 0.338 | 0.267 | 0.468 | 0.211 | 0.294 | 0.119 | 0.320 | 0.536 | 0.250 |
| Trp-Arg | 0.045 | 0.431 | 0.262 | 0.307 | 0.246 | 0.285 | 0.205 | 0.283 | 0.075 | 0.337 | 0.463 | 0.258 |
| Trp-Leu | 0.063 | 0.531 | 0.296 | 0.332 | 0.242 | 0.411 | 0.207 | 0.293 | 0.095 | 0.320 | 0.459 | 0.291 |

TABLE 4

| Substrate | Control Average | ASD Average | P value (Mann-Whitney) | Comment |
|---|---|---|---|---|
| a-D-Glucose | 2.045 | 1.580 | 0.092 | Not significant |
| Empty | 0.498 | 0.283 | 0.001 | Lower |
| L-Trptophan | 0.490 | 0.263 | 0.000 | Lower |
| Trp-Gly | 0.535 | 0.279 | 0.000 | Lower |
| Trp-Lys | 0.588 | 0.348 | 0.000 | Lower |
| Trp-Ala | 0.550 | 0.310 | 0.001 | Lower |
| Trp-Arg | 0.496 | 0.266 | 0.000 | Lower |
| Trp-Leu | 0.499 | 0.295 | 0.000 | Lower |

Assays designed on leukocytes have the potential to provide results more quickly than those designed on lymphoblasts. Leukocytes were prepared from blood on the same day or no more than one day after sampling. White cells were extracted from the buffy coat obtained after density gradient centrifugation. According to laboratory references, there are 4,000-10,000 leukocytes per mm$^3$, which is 4-10 million per ml (or cc). About 300,000 cells or about 0.03-0.075 ml of blood can be utilized in a testing protocol. White cells can be synchronized in order to have a high number of viable cells in the same part of the cell cycle.

These and other modifications and variations to the present disclosure may be practiced by those of ordinary skill in the art, without departing from the spirit and scope of the present disclosure. In addition, it should be understood the aspects of the various embodiments may be interchanged, either in whole or in part. Furthermore, those of ordinary skill in the art will appreciate that the foregoing description is by way of example only, and is not intended to limit the disclosure.

What is claimed is:

1. A method for diagnosing autism spectrum disorder, the method comprising:
   deriving a cell sample from a test subject, the cells of the cell sample comprising lymphoblastoids derived from the test subject or leukocytes taken from the test subject;
   culturing the cell sample in a culture medium, wherein the only energy source for the cells of the cell sample within the medium comprises tryptophan; and
   determining the presence or quantity of a marker in the culture medium, wherein the marker is a nicotinamide adenine dinucleotide;
   wherein a decrease in the quantity of the marker or lack of the presence of the marker in the culture medium as compared to a control value for non-affected individuals is an indication that the test subject is affected with autism spectrum disorder.

2. The method according to claim 1, wherein the cell sample comprises cells obtained directly from the subject.

3. The method according to claim 1, wherein the cell sample comprises cells of a cell line developed from cells obtained directly from the subject.

4. The method according to claim 1, wherein the cells are lymphocytes.

5. The method according to claim 1, wherein the cells are leukocytes.

6. The method according to claim 1, wherein the step of deriving a cell sample from a test subject comprises obtaining a blood sample from the test subject.

7. The method according to claim 1, wherein the energy source comprises isolated tryptophan.

8. The method according to claim 1, wherein the energy source comprises a tryptophan dipeptide.

9. The method according to claim 8, wherein the tryptophan dipeptide is tryptophan-glycine, tryptophan-lysine, tryptophan-alanine, tryptophan arginine, or tryptophan-leucine.

10. The method according to claim 1, wherein the nicotinamide adenine dinucleotide is the reduced form of the dinucleotide.

11. The method according to claim 1, wherein the nicotinamide adenine dinucleotide is phosphorylated.

\* \* \* \* \*